United States Patent [19]

Chin et al.

[11] Patent Number: 5,281,238
[45] Date of Patent: Jan. 25, 1994

[54] ENDOSCOPIC LIGATION INSTRUMENT

[76] Inventors: Albert K. Chin, 2021 Newell Rd., Palo Alto, Calif. 94303; Frank T. Watkins, 440 Santa Rita Ave., Menlo Park, Calif. 94025

[21] Appl. No.: 25,912

[22] Filed: Mar. 3, 1993

Related U.S. Application Data

[63] Continuation of Ser. No. 796,722, Nov. 22, 1991, abandoned.

[51] Int. Cl.⁵ ............................................. A61B 17/00
[52] U.S. Cl. .................................... 606/148; 606/139; 606/113
[58] Field of Search ............. 606/103, 139, 144, 148, 606/110-113, 228, 233; 206/363

[56] References Cited

U.S. PATENT DOCUMENTS

| | | | |
|---|---|---|---|
| 2,131,321 | 9/1938 | Hart | 606/139 |
| 3,476,114 | 11/1969 | Shannon et al. | |
| 3,476,115 | 4/1968 | Graeff et al. | |
| 4,018,229 | 4/1977 | Komiya | 606/139 |
| 4,935,027 | 6/1990 | Yoon | 606/148 X |
| 5,002,563 | 3/1991 | Pyka et al. | 606/222 |
| 5,082,112 | 1/1992 | Dunklee | 206/363 |

OTHER PUBLICATIONS

Ethicon, Johnson & Johnson, *Endoscopic Knot Tying Manual*, 1991.

*Primary Examiner*—Stephen C. Pellegrino
*Assistant Examiner*—Jeffrey A. Schmidt
*Attorney, Agent, or Firm*—Heller, Ehrman, White & McAuliffe

[57] ABSTRACT

An improved endoscopic ligature provided with a loop support means for stabilizing the shape, position and orientation of a suture loop. The stabilized loop is impervious to surface tension forces created by body fluids and will not close on itself or stick to moist surfaces. When the loop is cinched closed it dislodges from the support. The loop support is made of a flexible material with shape memory and has an unstressed width greater than that of the trocar cannula. The loop support is collapsible to allow the instrument to be inserted and withdrawn through the cannula.

21 Claims, 3 Drawing Sheets

ENDOSCOPIC LIGATION INSTRUMENT

This is a continuation of application Ser. No. 07/796,722 filed Nov. 22, 1991, now abandoned.

FIELD OF THE INVENTION

This invention relates to surgical instruments, and in particular endoscopic surgical instruments. Specifically, this invention relates to endoscopic suturing and ligating instruments.

BACKGROUND OF THE INVENTION

The last decade has seen dramatic advances in the field of endoscopic instrumentation, and the application of endoscopic techniques to a growing number of surgical procedures. The benefits—reduced pain and discomfort, shortened recovery time and better cosmetic results—insure that endoscopic surgery will continue to be a rapidly developing and widely applied technique.

Endoscopic surgery is performed with elongated instruments inserted through small holes in the skin, and is viewed through a video monitor. Therefore, such operations require more mental and physical dexterity than corresponding traditional surgical techniques. Because of these additional difficulties it is important to provide surgical tools that are as trouble free and easy to use as possible.

In endoscopic suturing, the knot must be secure and should be as small as possible to prevent tissue reaction. Stress to the suture weakens its strength and should be minimized. Any crimping or crushing of the suture, or any "sawing" between strands during the knot tying process is to be avoided. If the suture must pass through tissue the knot tying can be done extracorporeally or intracorporeally. If ligation is required a slipknot can be tied in the suture beforehand. Ligation is clearly the simpler suturing technique and therefore the method of choice when there is an option. Endoscopic ligatures are used to ligate vessels and tissue pedicles and to close the openings of cystic structures to prevent spillage contamination.

The state of the present technology in endoscopic ligating instruments is represented by the ENDOLOOP TM manufactured by Ethicon, a Johnson & Johnson Company, and the Surgitie TM Ligating Loop manufactured by Auto Suture Company, a division of United States Surgical Corporation. These endoscopic ligating instruments have an elongated bored staff with a suture threaded therethrough, the suture forming a loop at the intracorporeal end of the staff. The trocar is provided with a seal mechanism which can form an air-tight seal with the instrument upon insertion of the instrument into the cannula of the trocar. The segment of the staff extending past the seal remains outside the body during surgery and is used as a handle to position the loop. At the extracorporeal end of the staff the suture is connected to a short pull rod that is bonded to the staff. The bond is easily broken by a manual force. The loop is closed by pulling the rod away from the staff.

The instrument is used by placing the loop next to a tissue pedicle or vessel, gripping the tissue with a grasping tool, pulling the grasped tissue through the loop and tightening the loop by separating the pull rod from the staff and pulling it away from the staff.

A drawback of these instruments is that the flexibility of the suture necessary for ligature purposes makes the position and configuration of the loop susceptible to surface tension forces exerted by body fluids. In particular, the surface tension can cause a suture to collapse on itself, closing the loop. It is then difficult to reopen the loop with endoscopic tools, and such manipulations present the risk of inadvertently stressing the suture. Also a wetted suture will tend to adhere to wet surfaces, making it difficult to position the loop in close proximity to tissue. This problem is compounded by the fact that when the suture is wetted, the moisture softens the material. Gut suture is somewhat more impervious than braided Nylon or silk to this softening problem.

SUMMARY AND OBJECTS OF THE INVENTION

The present invention is directed to an improved endoscopic ligature which solves the above-mentioned problems and provides other advantages. The ligature of the present invention has a loop support means which can open the suture loop to a width greater than the width of the cannula, and can be contracted to a width less than the diameter of the cannula for insertion and extraction. The loop support prevents the loop from collapsing due to surface tension forces, and aids in the positioning and orientation of the loop by stiffening the loop so it will not stick to wet surfaces. Upon tightening the loop, the suture disengages from the support.

Therefore, an object of the present invention is to provide an endoscopic ligature with a suture loop that is impervious to surface tension forces induced by body fluids. In particular it is an object of the invention to provide a suture ligature which is easy to position and orient and will not inadvertently collapse on itself. Further objects and advantages of this invention will become apparent upon review of the following specification and claims.

DETAILED DESCRIPTION OF THE INVENTION

Figure 1:
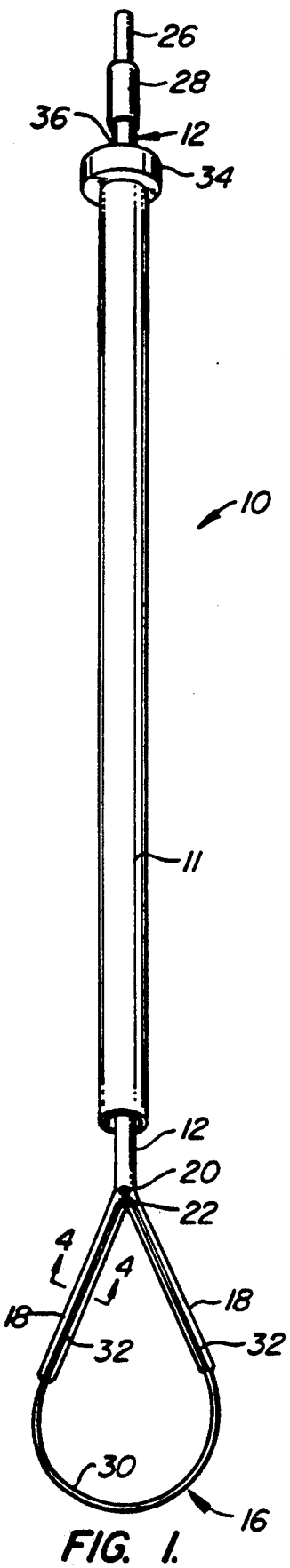
FIG. 1 shows the endoscopic ligature of the present invention with the suture loop retained by the loop support prongs and the pull rod engaged to the staff.
Figure 3:
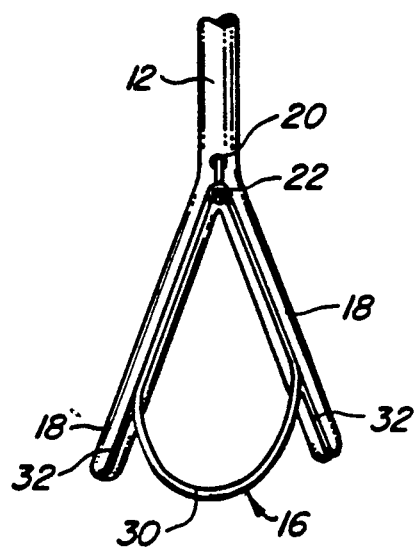
FIG. 3 is an enlarged fragmentary view of the suture loop partially disengaged from the support prongs.
Figure 4:
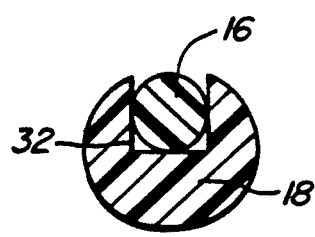
FIG. 4 is a cross sectional view of a support prong with the suture engaged in the retaining groove.

As shown in FIG. 1, the endoscopic ligature tool 10 of the present invention is comprised of a gut suture 16 which extends through a bore 20 in an elongated staff 12. The staff has a length of approximately 9", and a width of approximately ⅛. A loop 30 in the suture 16 at the intracorporeal end of the staff 12 is secured with a sliding knot 22. The aperature of the bore 20 at the intracorporeal end has a diameter greater than the diameter of the suture 16 but smaller than the width of the knot 22 so that the know 22 cannot enter the bore 20. Two flexible support prongs 18 protrude from the intracorporeal end of the staff 12, deviating from the longitudinal axis of the staff 12 with an angle of approximately 20 degrees. The prongs 18 have a length of approximately 1.5". Each prong 18 has a groove 32 along the length of the prong 18 with a width and depth suitable for a dislodgable friction fit with the suture 16 as shown in FIGS. 1 and 3, and in cross-section in FIG. 4. In another preferred embodiment (not shown) the width of the groove 32 near the opening is narrower than the width of the suture 16, so that the groove 32 distorts as the suture 16 is dislodged. In the preferred embodiment the staff 12 and support prongs 18 are made of plastic, e.g. polyvinyl chloride.

Figure 2:
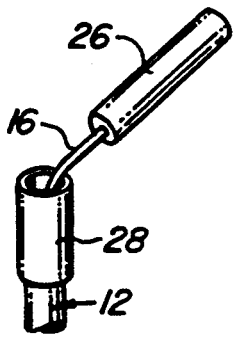
FIG. 2 is an enlarged fragmentary view of the pull rod separated from the retaining tubing and staff.

The extracorporeal end of the suture 16 is attached to an end of a pull rod 26. The pull rod 26 has a diameter approximately equal to that of the staff 12. The pull rod 26 is removably secured to the end of the staff 12 by a piece of elastomeric retaining tubing 28, preferably composed of polyolefin material. The tubing 28 fits snugly over a short length of the extracorporeal end of the staff 12 and a short length of the pull rod 26 at the end attached to the suture 16. A small manual force produces the separation of the pull rod 26 from the staff 12 as shown in FIG. 2.

Disengaging the pull rod 26 and pulling it 26 away from the staff 12 pulls the suture 16 through the staff 12. When the knot 22 abuts the aperature of the bore 20 the suture loop 30 begins to pass through the knot 22, reducing the size of the loop 30. When the diameter of the loop 30 is approximately equal to the distance between the ends of the support prongs 18 the suture 16 begins to disengage from the grooves 32 as shown in FIG. 3.

As shown in FIG. 1, the majority of the length of the staff 12 is surrounded by a substantially cylindrical sheath 11. Preferably, the sheath 11 is made of a plastic such as polyvinyl chloride, though other types of materials may be used. The sheath 11 has a diameter less than that of the cannula 44 of the trocar (depicted in FIG. 6 and discussed below). The extracorporeal end of the sheath 11 has a rubber cap 34. The staff 12 passes through an aperture 36 in the rubber cap 34 with a diameter slightly less than that of the staff 12. The contact between the staff 12 and the aperture 36 provides an air-tight seal while still allowing the position of the staff 12 in relation of the sheath 11 to be longitudinally adjusted. The sheath 11 can be engaged by the seal mechanism of the trocar (not shown) to prevent intracorporeal gases and fluids from escaping through the cannula 44 during surgery.

Figure 5:
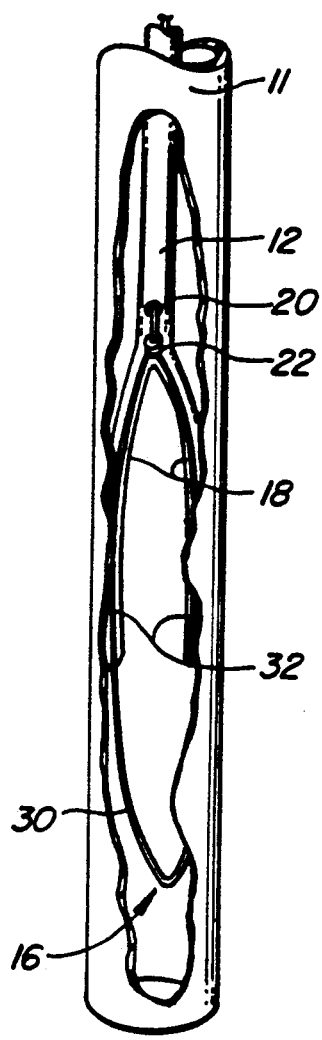
FIG. 5 shows the ligature with the suture loop and support prongs retracted into the sheath.

Retracting the intracorporeal end of the staff 12 into the sheath 11 forces the support prongs 18 to bend towards the longitudinal axis of the staff 12, as shown in FIG. 5. Because the cannula 44 has a diameter approximately equal to that of the sheath 11, the loop support prongs 18 must be retracted before the intracorporeal end of the ligature 10 can pass through the cannula 44.

Ligation with the present invention is straightforward and free of loop positioning and orientation problems. Access to the surgical region is obtained by puncturing the skin 48 (see FIG. 6) and other selected intervening tissues with a trocar. Preferably the sharp puncturing tip (not shown) of the trocar retracts into the trocar cannula 44 and 46 after puncturing the selected tissues to avoid damage to other tissues, vessels and organs. The cannula 44 or 46 is left in place during surgery to provide a conduit for endoscopic surgical instruments to the surgical region.

Initially segments of the loop 30 are retained by the grooves 32 in the support prong 18. The ligature 10, with the loop 30 and support prongs 18 retracted into the sheath 11 as shown in FIG. 5, is inserted into the cannula 44 of the trocar. The seal mechanism (not shown) of the trocar is then engaged to the sheath 11 to provide an air-tight seal between the internal surgical cavity and the outside. The loop 30 and support prongs 18 are then forced out of the sheath 11 by pushing the staff 12 a short distance through the aperture 36 in the rubber cap 34. The support prongs 18 have shape memory and outside the sheath 11 they spread apart, opening the loop 30 as shown in FIG. 6.

Figure 6:
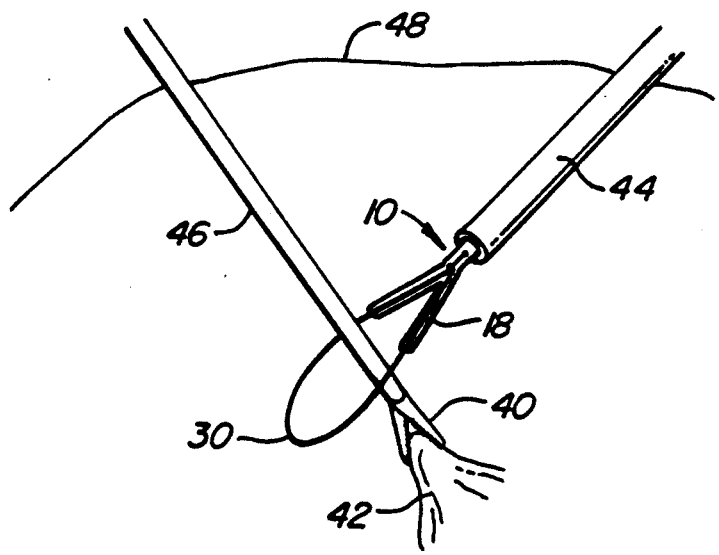
FIG. 6 depicts the ligature being used to ligate a tissue.

In FIG. 6 a grasping tool 40 which has been inserted into the body through a second cannula 46 which penetrates the skin 48 of the patient. The grasping tool 40 passes through the loop 30 and has grasped a body tissue 42. Because the support prongs 18 retain the loop 30 in an open configuration and maintain the orientation of the loop 30, the loop 30 is impervious to surface tension forces from body fluids. Therefore, the surgeon need not try to prevent the loop 30 of the endoscopic ligature 10 from coming into contact with moisture while positioning the loop 30 or performing other manipulations.

Once the tissue 42 is drawn through the loop 30 the loop 30 is cinched closed by separating the pull rod 26 from the staff 12 and pulling. This draws the knot 22 against the aperature of the bore 20 at the intracorporeal end of the staff 12, and thereafter causes the suture 16 material in the loop 30 to be drawn through the knot 22. When the width of the loop 30 becomes smaller than the distance between the ends of the support prongs 18 the suture 16 begins to dislodge from the support grooves 32. When the loop 30 has ligated the tissue 42 the remainder of the suture 16 still within the groove 32 can be easily dislodged by pulling the end of the staff 12 away from the ligated tissue 42 or pulling the suture 16 away from the support prongs 18 with the grasping tool 40. The suture 16 is cut approximately ¼" from the knot 22. The tool 10 can then be withdrawn through the cannula 44 after retracting the support prongs 18 into the sheath 11 by pulling the staff 12 through the aperture 36 in the extracorporeal direction.

Figure 7:
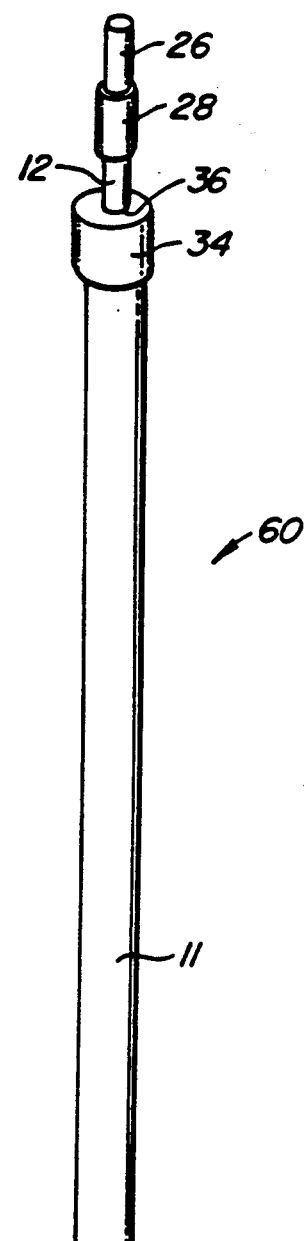
FIG. 7 displays another embodiment of the present invention where the suture loop is retained by a curved armature.
Figure 7:
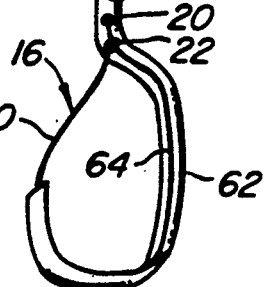
Figure 8:
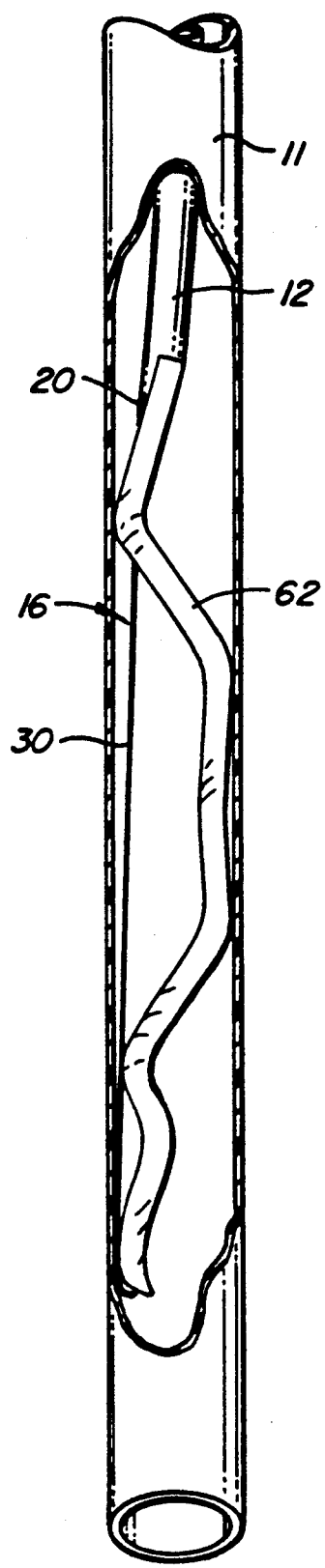
FIG. 8 displays the ligature of the second embodiment with the armature retracted into the sheath.

Another embodiment 60 of the present invention is depicted in FIG. 7. In this embodiment 60 the suture loop support means is a curved armature 62 extending from the extracorporeal end of the staff 12. The suture 16 passes through a bore 20 which extends through the staff 12 from the extracorporeal end of the staff 12 to just before the armature 62. A slip knot 22 which closes the loop 30 at the intracorporeal end of the suture 16 has a width greater than the width of the bore 20 at its intracorporeal end. The suture loop 30 is fastened to the armature 62 by a friction fit in a retaining groove 64 along the interior surface of the armature. The components at the extra corporeal end of this embodiment 60 are the same as the components of the first embodiment 10 with the same interrelations, and the same reference numerals are used. The width of the armature 62 is greater than the width of the sheath 11 or the staff 12. The armature 62 is flexible so as to allow it 62 to be retracted into the sheath 11 as shown in FIG. 8 by pulling the staff 12 through the aperture 36 in the rubber cap 34 in the extracorporeal direction. In the preferred embodiment the staff 12 and armature 62 are made of plastic, e.g. polyvinyl chloride.

The steps followed in the use of this ligature 60 are the same as for the first embodiment 10, and the reference numerals associated with the cannula 44, the grasping tool 40 and the ligated tissue 42 depicted in FIG. 6 are retained in this discussion. With the armature 62 retracted into the sheath 11 as shown in FIG. 8, the ligature 60 is inserted through the cannula 44 of the trocar into the body of the patient. The seal mechanism of the trocar (not shown) engages the sheath 11 to provide an air-tight seal between the intracorporeal surgical cavity and the outside. Pushing the staff 12 through the aperture 36 in the intracorporeal direction pushes the armature 62 out of the sheath 11. Once free of the sheath 11, the armature 62 returns to the hook shape shown in FIG. 7 and the loop 30 is open and ready for ligation. Once a pedicle or vessel 42 is drawn through the loop 30 with a grasping tool 40, the loop 30 is cinched closed by separating the pull rod 26 from the staff 12 and pulling. A segment of the suture 16 which remains lodged in the retaining groove 64 can be dislodged by either moving the staff 12 away from the ligated tissue 42 or pulling the suture 16 out of the groove 64 using the grasping tool 40. The suture 16 should be severed approximately ¼" from the ligation knot 22. Before withdrawal of the ligation instrument 60 through the cannula 44, the armature 62 must again be retracted into the sheath 11.

Figure 9:
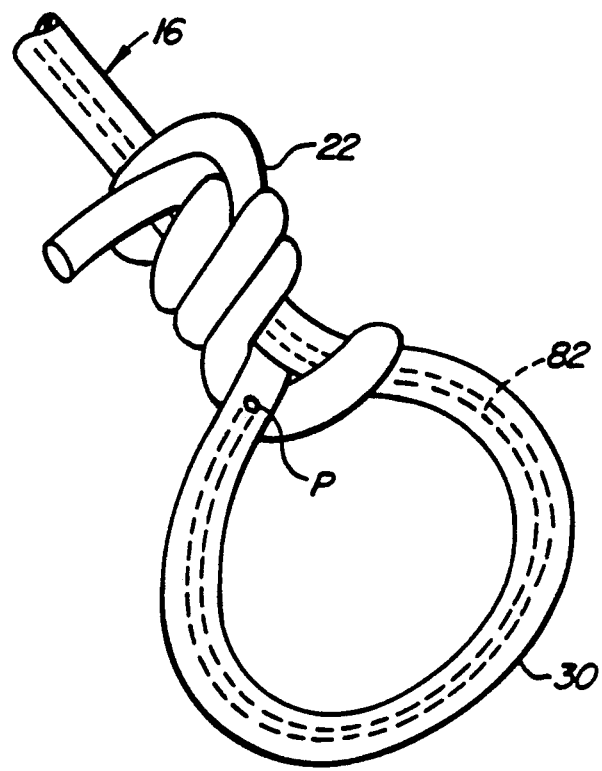
FIG. 9 is a view of the suture loop of an embodiment where the suture is supported by an internal wire.

FIG. 9 shows the intracorporeal end of a third embodiment 80 of the present invention. Components of this embodiment 80 which are the same as the components of the first embodiment 10 and have the same interrelations are referred to by the same reference numerals. In this embodiment 80 the gut suture 16 is supported by a thin support wire 82 (dotted lines) which runs through a bore in the middle of the suture 16. The wire 82 extends from the extracorporeal end of the suture 16 through the loop 30 to a point P just before the knot 22. The wire 82 may be made of spring steel, nitinol or some other material with shape memory. The wire 82 must have sufficient strength to make the suture loop 30 impervious to surface tension effects while still having sufficient flexibility to allow the suture 16 to be cinched closed and to be retracted into the sheath 11 for insertion of the instrument 80 through the cannula 44 of the trocar. The wire 82 is implantable (biologically unreactive) and can be left inside the patient.

When the pedicle or vessel 42 has been drawn through the loop 30 the suture 16 is cinched closed by dislodging the pull rod 26 from the rubber tubing 28 friction fitted to the end of the staff 12 and pulling the rod 26 in the extracorporeal direction. The suture 16 and support wire 82 are then severed approximately ¼' from the knot 22 once the tissue 42 has been ligated. Because the suture 16 which remains attached to the instrument 80 is essentially linear, the instrument 80 is easily withdrawn through the cannula 44 once ligation is completed. When the gut suture 16 eventually dissolves the ligation ceases since the support wire 82 did not extend around the entirety of the loop 30.

From the foregoing description it can therefore be seen that the present invention provides an improved endoscopic ligature which is easy to use and free of difficulties caused by surface tension forces acting on the suture loop. The suture loop of the present invention will not collapse on itself or stick to moist surfaces. Although the specifics of the preferred embodiments have been described in detail for clarity and understanding many other variations are possible. For instance, the ligature of the first embodiment could have the suture loop removably attached only to the ends of the support prongs or the pull rod may be removably fastened to the staff in a different manner; the suture in the second embodiment may be removably retained to the armature with a weak adhesive rather than a retaining groove; or the support wire in the third embodiment may be removed from the loop before cinching. The scope of the present invention should not be determined by the details of the specification but rather by the following claims.

What is claimed is:

1. An instrument for ligation through an endoscopic trocar cannula comprising:

an elongated suture support having an intracorporeal end, and extracorporeal end and a first longitudinal axis;

a suture having an intracorporeal end and an extracorporeal end, said suture extending along and supported by said elongated suture support, said suture having a cinchable loop at the intracorporeal end thereof;

a first adjustable elongated loop support mounted at the intracorporeal end of said elongated suture support, said first loop support having a second central longitudinal axis, said first loop support having a first elongated retaining groove with a third central longitudinal axis, a substantial portion of said loop being removably engageable in said first retaining groove, whereby said first loop support controls and stabilizes said loop when engaged therewith; and control means located at the extracorporeal end of said elongated suture support for selectively moving said first loop support between a first state and a second state, said second longitudinal axis being more closely aligned with said first longitudinal axis in said first state than in said second state, said third longitudinal axis paralleling said second longitudinal axis in said second state, and said second longitudinal axis being noncolinear with said first longitudinal axis in said second state.

2. The instrument of claim 1 further comprising a second adjustable elongated loop support mounted at the intracorporeal end of said elongated suture support, said second loop support having a fourth central longitudinal axis, said second loop support having a second elongated retaining groove with a fifth longitudinal axis, a substantial portion of said loop being removably engageable in said second retaining groove, whereby said second loop support controls and stabilizes said loop when engaged therewith.

3. The instrument of claim 2 wherein said control means selectively moves said second loop support between a third state and a fourth state, said fourth longitudinal axis being more closely aligned with said first longitudinal axis in said third state than in said fourth state, said fifth longitudinal axis paralleling said fourth longitudinal axis in said fourth state, and said fifth longitudinal axis being noncolinear with said first longitudinal axis in said fourth state.

4. The instrument of claim 3 wherein said first and second loop supports are substantially linear.

5. The instrument of claim 2 wherein said first and second loop supports are substantially nonlinear.

6. The instrument of claim 2 wherein said first and second retaining grooves are configured to frictionally retain said loop.

7. The instrument of claim 2 wherein said loop disengages from first and second loop supports when cinched.

8. The instrument of claim 1 wherein said first loop support is substantially linear.

9. The instrument of claim 1 wherein said first loop support is substantially nonlinear.

10. The instrument of claim 1 wherein said suture support is substantially tubular forming a bore, said bore housing a portion of said suture in a sliding relationship.

11. The instrument of claim 1 wherein said first retaining groove is configured to frictionally retain said loop.

12. An instrument for ligation through an endoscopic trocar cannula comprising:
    an elongated suture support having an intracorporeal end, an extracorporeal end and a first longitudinal axis;
    a suture having an intracorporeal end and an extracorporeal end, said suture extending along and supported by said elongated suture support, said suture having a cinchable loop at said intracorporeal end thereof, a first point on said loop being removably engageable near said intracorporeal end of said suture support;
    a first adjustable elongated loop support prong having a second longitudinal axis, a first distal end, and a first proximal end, and being mounted near said first proximal end to said intracorporeal end of said suture support, said loop being removably engageable to said first support prong at a second point near said first distal end thereof and a third point between said first distal and proximal ends thereof, whereby said first support prong controls and stabilizes said loop when engaged therewith; and
    control means located at said extracorporeal end of said suture support for selectively moving said first support prong between a first state and a second state, said second longitudinal axis being more closely aligned with said first longitudinal axis in said first state than in said second state, and said second longitudinal axis being noncolinear with said first longitudinal axis in said second state.

13. The instrument of claim 12 wherein said loop is removably engageable to said first support prong at a fourth point on said first support between said second and third points.

14. The instrument of claim 12 further comprising a second adjustable elongated loop support prong having a third longitudinal axis, a second distal end, and a second proximal end, and being mounted near said second proximal end to said intracorporeal end of said suture support, said loop being removably engageable to said second support prong at a fourth point near said second distal end thereof and a third point between said second distal and proximal ends thereof, whereby said second support prong controls and stabilizes said loop when engaged therewith.

15. The instrument of claim 14 wherein said control means selectively moves said second support prong between a third state and a fourth state, said third longitudinal axis being more closely aligned with said first longitudinal axis in said third state than in said fourth state, and said third longitudinal axis being noncolinear with said first longitudinal axis in said fourth state.

16. The instrument of claim 15 wherein said first and second support prongs are substantially linear.

17. The instrument of claim 15 wherein said first and second support prongs and said suture support are formed integrally.

18. The instrument of claim 15 wherein said suture support is generally tubular forming a bore, said bore housing a portion of said suture.

19. An instrument for ligation through an endoscopic trocar cannula comprising:
    (a) an elongated suture support having an intracorporeal end and extracorporeal end;
    (b) a suture having an intracorporeal end and an extracorporeal end, said suture extending along and supported by said elongated suture support, said suture having a cinchable loop at the intracorporeal end thereof with a longitudinal bore therethrough;
    (c) an implantable support wire extending through said longitudinal bore for controlling and stabilizing said loop; and
    (d) a control means located at the extracorporeal end of said elongated suture support for selectively moving said loop between a collapsed state and an open state.

20. The instrument of claim 19 wherein said suture support is generally tubular forming a bore, said bore housing a portion of said suture in a sliding relationship.

21. The instrument of claim 19 wherein said cinchable loop is closed with a slipknot.

* * * * *

UNITED STATES PATENT AND TRADEMARK OFFICE
CERTIFICATE OF CORRECTION

PATENT NO. : 5,281,238
DATED : January 25, 1994
INVENTOR(S) : Albert K. Chin, et al.

It is certified that error appears in the above-indentified patent and that said Letters Patent is hereby corrected as shown below:

On the title page, after item (76): Inventor, insert the following:

--item (73): Assignee, Origin Medsystems, Inc., 135 Constitution Drive, Menlo Park, California 94025,--

Signed and Sealed this

Thirtieth Day of August, 1994

BRUCE LEHMAN

*Attest:*

*Attesting Officer*        *Commissioner of Patents and Trademarks*